United States Patent
Peyrard

(10) Patent No.: US 10,152,869 B2
(45) Date of Patent: Dec. 11, 2018

(54) PERSONAL SYSTEM FOR THE DETECTION OF A RISKY SITUATION AND ALERT

(71) Applicant: ELLCIE-HEALTHY, Nice (FR)

(72) Inventor: Philippe Peyrard, Antibes (FR)

(73) Assignee: ELLCIE-HEALTHY, Villeneuve Loubet (FR)

( * ) Notice: Subject to any disclaimer, the term of this patent is extended or adjusted under 35 U.S.C. 154(b) by 0 days.

(21) Appl. No.: 15/852,554

(22) Filed: Dec. 22, 2017

(65) Prior Publication Data

US 2018/0122208 A1 May 3, 2018

Related U.S. Application Data

(63) Continuation-in-part of application No. PCT/FR2017/051362, filed on May 31, 2017.

(51) Int. Cl.
| | |
|---|---|
| *G08B 21/04* | (2006.01) |
| *G06F 3/01* | (2006.01) |
| *A61B 5/00* | (2006.01) |
| *A61B 3/00* | (2006.01) |
| *A61B 8/00* | (2006.01) |
| *A61B 5/0205* | (2006.01) |
| *A61B 5/11* | (2006.01) |

(Continued)

(52) U.S. Cl.
CPC .......... *G08B 21/043* (2013.01); *A61B 5/6803* (2013.01); *G06F 3/013* (2013.01); *G08B 21/0446* (2013.01); *G08B 21/0453* (2013.01); *G08B 21/0476* (2013.01); *G08B 21/0492* (2013.01); *A61B 3/00* (2013.01); *A61B 5/02055* (2013.01); *A61B 5/1103* (2013.01); *A61B 5/1114* (2013.01); *A61B 5/14532* (2013.01); *A61B 5/18* (2013.01); *A61B 5/7445* (2013.01); *A61B 5/7455* (2013.01); *A61B 8/00* (2013.01); *A61B 2503/22* (2013.01); *A61B 2560/0242* (2013.01); *A61B 2562/0219* (2013.01)

(58) Field of Classification Search
CPC ................ G08B 21/06; G08B 21/0446; G08B 21/0453; G08B 21/0469; G08B 21/0492
See application file for complete search history.

(56) References Cited

U.S. PATENT DOCUMENTS

| | | | | |
|---|---|---|---|---|
| 5,689,241 | A * | 11/1997 | Clarke, Sr. ............... | A61B 5/18 340/575 |
| 2001/0005230 | A1* | 6/2001 | Ishikawa ................ | H04N 5/232 348/333.03 |

(Continued)

FOREIGN PATENT DOCUMENTS

EP 2 061 026 A1 5/2009

*Primary Examiner* — Hongmin Fan
(74) *Attorney, Agent, or Firm* — Im IP Law; C. Andrew Im; Chai Im

(57) ABSTRACT

A system and a method implementing such a system. The system includes eyeglasses having hinged stems, a plurality of sensors and an alert alarm. The system further includes a triaxial accelerometer, an IR transmitter, an IR receiver, and a barometric sensor. The sensors are set up in the hinged stems and the rims of the eyeglasses and connected to a processing and calculation unit. The processing and calculation unit includes a microprocessor and a memory. The processing and calculation unit executes a computer program to analyze data issued by the sensors and triggers the alarm based on a result of the analyzed data.

12 Claims, 8 Drawing Sheets

(51) Int. Cl.
    *A61B 5/145*    (2006.01)
    *A61B 5/18*    (2006.01)

(56) References Cited

U.S. PATENT DOCUMENTS

| | | | |
|---|---|---|---|
| 2001/0028309 A1 | 10/2001 | Torch | |
| 2004/0000733 A1* | 1/2004 | Swab | H04W 56/0015 264/1.7 |
| 2009/0105605 A1 | 4/2009 | Abreu | |
| 2010/0134761 A1 | 6/2010 | Johns et al. | |
| 2013/0010256 A1* | 1/2013 | Haddock | G02C 5/2272 351/159.31 |
| 2013/0125406 A1* | 5/2013 | Delort | G02C 13/003 33/200 |
| 2013/0197856 A1* | 8/2013 | Barfield | G01P 15/00 702/141 |
| 2015/0354941 A1* | 12/2015 | Heaton | A61B 5/0059 607/48 |
| 2016/0178904 A1* | 6/2016 | Deleeuw | H04N 13/044 345/8 |
| 2016/0262608 A1* | 9/2016 | Krueger | A61B 3/0041 |
| 2017/0061758 A1* | 3/2017 | Sudo | G08B 19/00 |

* cited by examiner

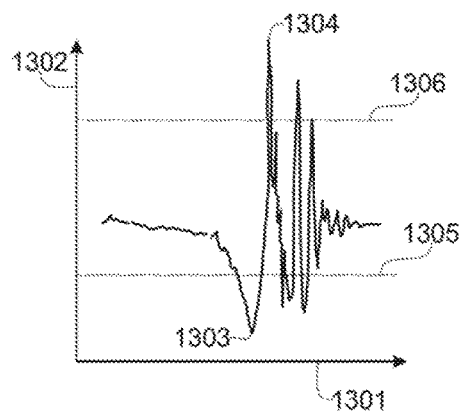
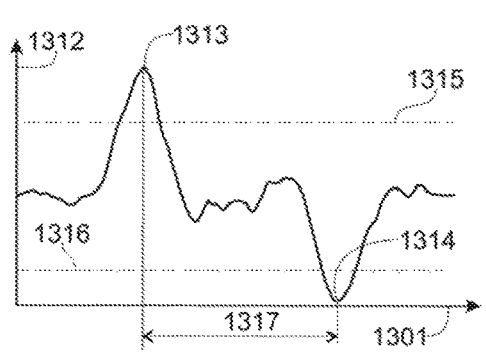
Fig. 13A
Fig. 13B
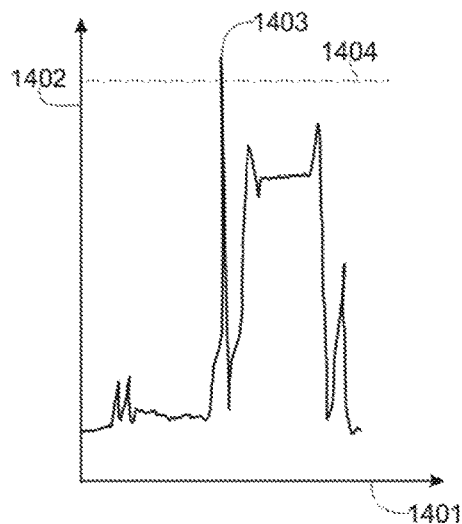
Fig. 14

PERSONAL SYSTEM FOR THE DETECTION OF A RISKY SITUATION AND ALERT

FIELD OF THE INVENTION

The invention is about a personal system for the detection of a risky situation and alert. The invention belongs to the field of portable devices capable of measuring physiological data of an individual.

BACKGROUND OF THE INVENTION

As non-limiting examples, such a risky situation involves cases of reduced alertness, following drowsiness or a loss of consciousness, or falling cases. The effects of a drop of alertness are likely to have serious consequences when the person experiencing it drives a vehicle or a machine, the risk extending to the passengers of the vehicle or to the facilities and people close to the machine. Even a light fall, may potentially be a vital hazard when it affects an elderly or a disabled person. The risks involved in these situations are significantly reduced if suitable measures are completed on time. Thus, as a for instance, the driver a vehicle easily overestimates its state of alertness, to the point of getting caught by a real slumber. A simple alarm directed to his intention or to the passengers in the vehicle allows to make him aware of his drowsiness state and to foster him to stop driving. The harmful consequences of a falling, even heavy, are mitigated if assistance is provided to the person in a short time. Other comparable cases concern, for example, seizures.

In the US, 4% —approximately eleven million drivers—admit they have had an accident or near accident because they dozed off or were too tired to drive. According to data from Australia, England, Finland, and other European nations, drowsy driving triggers 10 to 30 percent of all crashes. Falls are the leading cause of death in people over 65. Every second of every day in the United States an older adult falls, making falls the number one cause of injuries and deaths from injury among older Americans. In 2014 alone, older Americans experienced 29 million falls causing seven million injuries and costing an estimated $31 billion in annual Medicare costs. Besides death cases, people who are victims of a fall usually experience a loss of autonomy and a loss of self-confidence that also have important consequences. Studies show that, in the case of an elderly person, the longer the time spent on the ground after a fall, the more serious the consequences. Alertness disorders may also cause a fall, they are the result of e.g. an extreme fatigue, or more commonly the result of drugs or alcohol consumption. Thus, in some instances, the detection of a loss of alertness and the warning of the person experiencing it or of one of his relatives, may prevent a fall.

Physiological measurements performed on groups of individuals in laboratory conditions, can statistically detect signs of reduced alertness, sleep, fall or loss of consciousness. These tests use multiple sensors that can be worn by an individual only in laboratory conditions. When the results of these experiments are used with the aim of developing a personal detection device, the detection quality usually drops, for various reasons, including:
- it is difficult to integrate suitable sensory, in terms of the number of sensors and their reliability of measurement, in a wearable device;
- the wearable device is unsightly, uncomfortable, too intrusive or too perceived by the individual and his relatives as a surveillance device, so that the individual does not wear it;
- the detection reliability is not satisfactory, because of the reduced number of sensors and owing to the fact that it is based on statistical data not adapted to the individual itself and his way of life, and leads to the generation of false alarms, so that the person loses her confidence in the device and does not wear it anymore;
- the detection is too late, as a for instance, a system detecting drowsiness by a continuous closing of the eyes, during one second or more, or by the detection of a head drop, detects in fact an advanced stage of drowsiness. If this detection, and possible actions that it triggers is of certain utility, a car launched at 80 mph (130 km/h) travels 118 feet (36 meters) in one second, what significantly reduces the effectiveness of any maneuver carried out by the driver, thus woken up in a critical situation;
- the detection system usually uses cascading tests where the outcome of a first test determines the implementation of a second test, etc. . . . when reliability is poor it only gets worse from one test to the other and generates positives false or negatives false;
- the autonomy of the personal system is low because of the power consumption of the many components and of the required computing power.

The invention aims to solve the disadvantages of the prior art by offering a system based on an aesthetic sensor, autonomous and lightweight, specifically suited to its user.

OBJECT AND SUMMARY OF THE INVENTION

To this end the invention pertains to a system comprising a pair of eyeglasses with hinged stems and including a plurality of sensors and means of alarm, comprising:
- a triaxial accelerometer;
- a transmitter and a receiver of infrared light;
- a barometric sensor;
- said sensors being set in the stems and the rims and being connected to a processing and calculation unit comprising:
- a microprocessor and memory means;
- the processing and calculation unit comprising a computer program for the analysis of data issued by the sensors, and the trigger of the means of alarm, based on the analysis of these data.

The sensors, thus arranged at the level of the head of the individual wearing the pair of eyeglasses of the system the invention, are necessary and sufficient to detect a loss of alertness and its consequences, including a hard or soft fall, and when appropriate, the state of alertness after the fall, discriminating positive false and negative false from real alarms by an appropriate processing of information issued by the sensors, said processing being also the subject of the invention. The system may also comprise additional sensors according to specific embodiments. However, the use of a small number of sensors for the detection of a complex situation by a smart processing of the signal, allows a reduced power consumption and a broad operation autonomy, while maintaining a light weight for wearing comfort. The installation of such sensors in a pair of classic eyeglasses, with foldable stems, enables the individual to wear the device of the invention in a discreet and aesthetic way. As compared to other personal systems of detection, such as wristbands or medallions, the installation of sensors in a pair of eyeglasses favors a nearly continuous wearing of said sensors by the user during its hours of activity, most of users being used to wear their eyeglasses as soon as they wake up.

Throughout the text the term 'or' must be interpreted as inclusive (and/or).

The invention is advantageously implemented according to embodiments and variants exposed hereunder, which are to be considered individually or in any technically operative combination.

According to a specific embodiment, the processing and calculation unit is also carried by the pair of eyeglasses of the system of the invention. Thus, the device is autonomous and does not require any extra accessory to work.

According to another embodiment that is compatible with the previous one, the eyeglasses comprise means of wireless connection able to exchange information with a remote connected unit. This embodiment makes it possible to move all or part of the processing and calculation means as well as alarm means to an additional separate device. Pertaining to this embodiment to eyeglasses of the system of the invention is then said to be connected.

According to an exemplary embodiment the remote unit is a smartphone. Thus, in addition to the extra computing power provided by the resources of the smartphone, the latter is able to communicate through various networks to servers or remote recipients, in order to either share with them measured data or to trigger alarms and actions in response to a given situation.

Advantageously, the system comprises of a central server and the processing and calculation unit comprises means for internet access and is capable of exchanging information with the server. Thus, the data collected by the central server makes it possible, by an appropriate processing of these data, to improve and to upgrade the processing algorithm, and to update the computer program of the processing and calculation unit, by a communication between the central server and said unit.

According to an embodiment, the lenses of the spectacles are mounted in rims separated by a bridge, the transmitter and the receiver being set on the edge of a rim so as to be directed towards the eye, the transmitter being positioned in the lower outer part of the rim, distal from the bridge, and the receiver on the upper part of the rim close to the stem hinge. This arrangement allows the most reliable detection of eye blinks and eyelid closure whatever of the direction of the gaze. Advantageously, this same arrangement is replicated on each of the rims of the eyeglasses.

Advantageously, the eyeglasses comprise an electronic board housed inside each of the stems and a wired connection between each electronic board, said wired connection extending inside the upper side of the rims and the bridge. Thus, the lower parts and the inner portions of the rims, are free from any electronics or sensors, allowing the mount of the lenses with optician's conventional techniques.

Advantageously, the stems of the eyeglasses comprise a aft part, without any electronic means, that is mechanically connected to a front part of the stems, said aft part being suitable for being adapted to the morphology of the individual wearing the eyeglasses.

Advantageously, the hinges of the stems of the eyeglasses comprise a passageway for the wired connection.

Advantageously, the triaxial accelerometer is placed substantially in the middle of a stem. Thus, it is positioned substantially centered over the wearer's head and allows a more reliable detection of its movements.

Advantageously, the eyeglasses comprise a battery mounted in one of the stems, and the electronic board, the processing and calculation unit, the battery and the sensors are positioned in the front part of the eyeglasses. The front part of the eyeglasses substantially extends between the rims and the parts of the stems that are in front of the ears when the eyeglasses are worn. This configuration provides flexibility in the adaptation of the rear parts of the stems, whether with or without curved temple tip, to the morphology of the user, thus ensuring a comfortable wearing.

In a specific embodiment, the eyeglasses comprise at least one sensor among:
- a gyro sensor;
- a magnetic compass;
- a thermometer to measure body temperature;
- a blood pressure sensor;
- a blood glucose sensor;
- an oximetry sensor;
- a heart pace sensor.

By adding further sensors, the reliability of detection and the variety of detectable risky situations are enhanced as well of the prevention of such risky situations by obtaining physiological information relating to the individual from which typical early warning signs of such situations are extracted. As a for instance, the combination of a gyro sensor and a magnetic compass with the accelerometer allows an accurate quantification of postures according to 9 axes.

Advantageously, the sampling frequency of the signals from the sensors is set between 50 Hz and 150 Hz and preferentially set around 70 Hz. This 70 Hz acquisition frequency is high enough to allow a reliable detection, while low enough to limit the power consumption.

Also disclosed is a method for the detection of a risky situation threatening an individual and implementing the system of the invention in any of its embodiments, comprising any combination of the steps consisting in:
i. controlling the IR transmitter and collecting and processing signals from IR receiver to detect the wearing of the eyeglasses by the individual;
ii. controlling the IR transmitter and collecting and processing signals from the IR receiver to measure the state of alertness of the individual;
iii. collecting and processing signals from the triaxial accelerometer to detect a fall;
iv. collecting and processing signals from the barometric sensor in combination with information collected in step iii) to characterize the fall;
v. generating an alarm in response to the results of step ii), step iii) or step iv).

The arrangement of these different steps within algorithms contained in the program setup in the processing and calculation unit, enables the prevention, the detection and the discrimination of various risky situations, from the beginning of a loss of alertness up to a hard fall and a possible loss of consciousness, going through a slumber or a fall qualified as a soft fall.

Advantageously, step ii) of the method of the invention comprises a filtering of the signal received from the IR receiver to suppress the influence of ambient light on said signal. Advantageously said filtering consists in the application of a digital generalized moving average polynomial filter, followed by a band pass filter. Thus, the method and the system of the invention issue reliable information regardless of the lighting conditions in which the individual is immersed.

According to one embodiment, the processing of the collected signal in step ii) comprises the calculation of a composite index of alertness combining parameters comprising:

a. the relative duration of the masking of an eye of the individual by its eyelid on a first given time;
b. the average time interval between two successive eye blinks, over a second given time, in relation with a first reference that is specific to the individual;
c. the scattering of the ratio between the closing magnitude and the closing speed of the eyelid, over a third given time, in relation with a second reference that is specific to the individual;
d. the proportion of eye blink whose duration exceeds a certain threshold, over a fourth given time.

Thus, the use of a composite index of alertness, simultaneously integrating several factors of detection of a loss of alertness, allows to obtain an accurate assessment of the effective alertness of the individual. Among the considered parameters, parameters b) and c) are compared to specific individual references while parameters) and d) are indicators characterizing a state of alertness and a state of advanced drowsiness regardless of the individual.

Therefore, the first and the second references specific to the individual for a given period of time, may be calculated from the collection and the processing of the signals of the infrared receiver, and assessed when specific conditions involving the level of parameter a) or of parameter d) are met.

According to an embodiment of the method of the invention, step v) comprises the generation of an alertness alarm whose level is based on the results of step ii) and step iii). Thus, the method of the invention generates several levels of alarm pertaining to the severity of the loss of alertness up to a fall. According to exemplary implementations this fall corresponds to a head drop following a slumber, up to a body fall following, for example, a seizure.

According to one embodiment, the processing performed in steps iii) and iv) generates a composite index of severity of fall from parameters comprising:
t. the acceleration magnitude combined along the three axes of the triaxial accelerometer;
u. the variance of parameter t) over a given duration;
v. the acceleration component over the axis of the triaxial accelerometer parallel to the gravity.

The calculation and the combination of these parameters into a composite index, can detect a fall, and is also used to differentiate a fall of the body, generating one type of alarm, from a head drop that is used, as a for instance, for the detection of a slumber. The index of severity of fall is used to trigger or not to trigger an alarm relating to a fall.

Advantageously, the processing performed in steps iii) and iv) generates a composite index of severity of fall from parameters comprising:
w. the magnitude of acceleration, combined over the axes of the triaxial accelerometer in a plane perpendicular to the gravity;
x. the variation of the barometric pressure between two moments.

By adding these parameters to the ones defined above, a so-called soft fall can be detected, as a for instance, in the case of a fall of a person leaning against a wall while keeping its head in vertical position during the fall.

Using a composite index also enables to highlight real fall incidents with regard to situations arising in everyday life that could be falsely interpreted as a fall, such as, for example, stepping down a stairway.

Advantageously, the trigger of the fall alarm is conditioned by the level of an additional parameter assessed after the detection of the fall. The assessment of this parameter enables to discriminate a serious fall, causing a loss of consciousness, an injury or an inability of the person to recover, from a fall without harmful consequences, and thus to avoid the trigger of a needless alarm.

According to one embodiment, the parameter assessed after the fall detection comprises, alone or in any combination:
an assessment of the state of alertness according to step ii);
a measure of the posture of the individual using signals from the triaxial accelerometer or from the barometric sensor;
the time spent on the ground, using signals from the triaxial accelerometer and from the barometric sensor.

BRIEF DESCRIPTION OF THE DRAWINGS

The invention is described hereunder according to its preferred embodiments, in no way limiting, and with reference to FIGS. 1 to 15, in which:

FIGS. 13A-B show examples of evolution of signals during a fall event, FIG. 13A the signal issued by the accelerometer, FIG. 13B the signal issued by the barometric sensor;

FIG. 14 shows an example of the evolution of the acceleration in a plane perpendicular to gravity during a soft fall event.

DETAILED DESCRIPTION OF THE EMBODIMENTS

Figure 1:
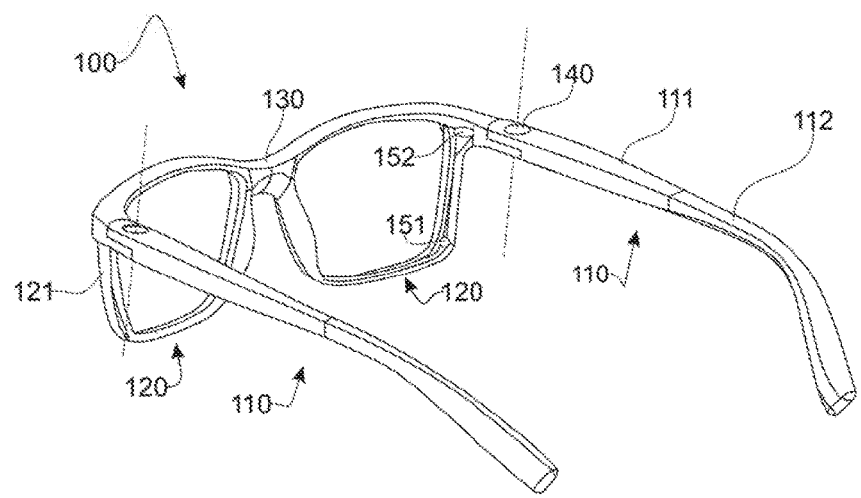
FIG. 1 is a perspective view of an exemplary embodiment of the eyeglasses of the system of the invention.

FIG. 1, according to an exemplary embodiment, sensors of the system of the invention are borne by a pair of spectacles (100), featuring two hinged stems (110), two rims (120) holding the prescription or not lenses, said rims (120) being linked by a bridge (130) resting on the nose of the user when the spectacles are worn. According to this exemplary embodiment, the stems comprise two parts. A first part (111), so-called front part, extends from the stem hinge (140) along about half of the stem length. The second part (112) of the stem, so-called aft part, is connected to the first part (111) e.g. by clipsing. This second part rests on the ear of the user, and include or not a curved temple tip, also called earpiece, pursuant to different styles of eyeglasses. According to this exemplary embodiment, the front part of the stem bears electronic modules, while the second part (112) does not include any electronics. Therefore, this second part is adapted to the morphology of a user like for any conventional eyeglasses, by using a shorter or a longer second part (112), or even by distorting it by heating. Similarly, the rims comprise two parts, the outer part (121) of the rims, extending substantially between the hinge and the basis of the rims, bears sensors, including an IR transmitter (151) and an IR receiver (152). The lower part and the inner part of the rims (120), up to the bridge (130), are free from any electronics and eases the mounting of any type of lens. According to this example, the rims are made of plastic and fully surround the lenses. As a for instance, the lenses are set up in the spectacles by heating the lower part of the rims and their connections to the bridge. However, the design of the spectacles of the system of the invention authorizes the use of other types of rims between the outer part (121) and the bridge (130), such as metallic rims or wire type rims. According to this exemplary embodiment the nose-pads are integrated to the rims and the bridge. However, the design of the spectacles, in the same way that it allows the fitting of other types of rims, also allows the setup of nose-pads hinged on pad arms, which then can be adjusted in the same way as for conventional eyeglasses. Therefore, the spectacles of the system of the invention are adaptable to the morphology of their user, like conventional eyeglasses, to achieve optimal wearing comfort and stability. The eyeglasses are therefore suited to any type of lenses, prescription or not, simple, bifocals or progressive, or simply fashionable. They allow, in addition, different variations of style to match their aesthetic with the taste of the user. The mounting of the lenses as well as the mechanical adjustments of the eyeglasses of the system of the invention are preferentially performed by a professional, e.g. an optician, according to known techniques, similar to the techniques used for conventional eyeglasses.

Electronic modules are distributed between the front (111) parts of the left and the right stems, and are connected by a flexible bus running through the upper parts of the rims and the bridge (130).

Figure 2:
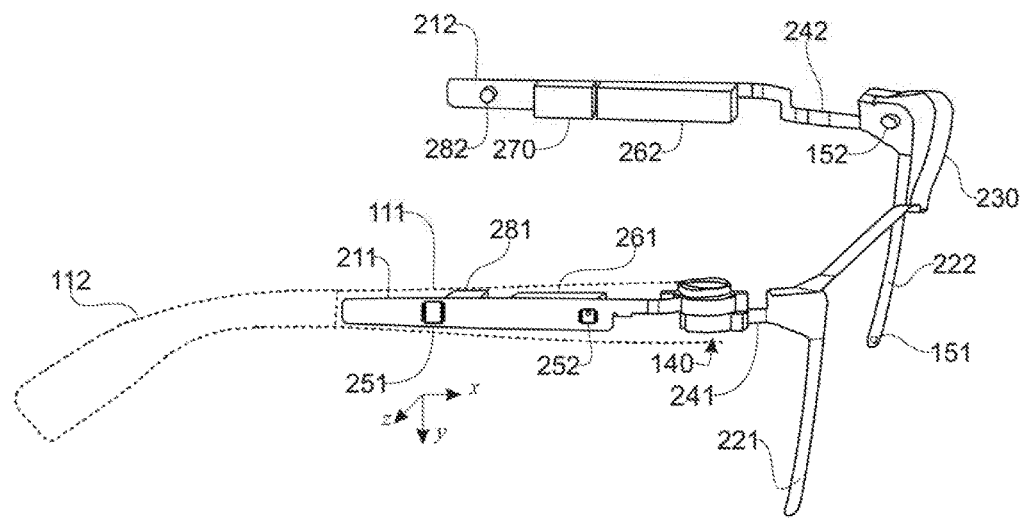
FIG. 2 shows in a perspective view, an exemplary embodiment of the arrangement of electronics within the frame of the eyeglasses of the system the invention.

FIG. 2, according to an exemplary embodiment, the eyeglasses of the system of the invention comprise several circuit boards (211, 212, 221, 222), on which the various sensors, acquisition and calculation means as well as data transmitting means, are welded or snapped. According to this exemplary embodiment, the electronic boards are housed inside the front part of the stems and inside of the outer parts of the rims. As a for instance, those parts of the stems and rims are made of a plastic material such as a polyamide or acetate or of a composite material comprising a thermosetting or thermoplastic matrix reinforced by a fibrous charge of glass or carbon, for more lightweight and strength. These envelopes provide both mechanical shielding and weather proof of the electronics, and are available in different colors, different surface textures and different shapes. The electronic boards (211, 212, 221, 222) are connected to each other by flexible buses (241, 242, 230), comprising a central bus (230) extending between the right side and the left side of the spectacles and running through the inside of the upper parts of the rims and the bridge, and side buses (241, 242) connecting the boards (211, 212) located inside the front parts of the stems and the boards (221, 222) located inside the outer edges of the rims. The side buses (241, 242) are running through the hinges (140) of the stems, said hinges being specifically designed for this purpose. Thus, the functions of measurement, signal processing, calculation, data transmission and power distribution are essentially distributed between the two stems, so as to balance the weight distribution between the two sides of the eyeglasses frame. The sensors used are of the ultra-miniaturized type also known as "MEMS" or "NEMS". According to one embodiment, the eyeglasses comprise an IR transmitter (151) and an IR receiver (152), set on an electronic board (222) within the outer edge of a rim. The transmitter and the receiver are oriented towards the eye of the user. In another embodiment, the same layout is set in both the left rim and the right rim. Doubling of the device allows for measurements on each eye in order to assess the consistency of the obtained signals, and to only use the signals issued by one of the transmitter-receiver couple, in the case of malfunction of the other. A triaxial accelerometer is set on one of the electronic boards included in the stems, i.e. on the electronic board (211) located in the right stem according to the exemplary embodiment shown in FIG. 2. The accelerometer measures accelerations in three directions (x, y, z). According to this non-limiting example, said accelerometer is mounted so that the acceleration of gravity is oriented pursuant to the positive y axis when the eyeglasses are worn by the user. According to another embodiment, the accelerometer sensor is included in a so-called inertial MEMS, comprising a triaxial accelerometer and a gyro sensor. According to yet another embodiment, the accelerometer is included in a MEMS, comprising a triaxial accelerometer, a gyro sensor and a magnetic compass. Advantageously, the sensor comprising the accelerometer includes an integrated temperature probe, making it possible to correct the signal gain and linearity according to the sensor temperature. As a non-limiting example, the accelerometer used in the system of the invention has an amplitude of measurement of $\pm 6$ g ($\pm 58.86$ ms$^{-2}$) on each axis. According to a specific embodiment, a second triaxial accelerometer is set on the electronic board (212) of the left stem of the eyeglasses. The combination of the two accelerometers signals allows to improve the accuracy of the measurement of rotational head movements and to better differentiate these movements from movements of the whole body of the user. The second accelerometer is preferably set on the other stem in symmetry with the first one. Head movements, like flexion-extension (movement of the sign "yes"), axial rotation (movement of the sign "no"), or of side inclination, result in particular in the accelerations projecting in opposed signs on the axes of the two accelerometers. Thus, for example, while referring to the (x, y, z) system of FIG. 2, a side inclination results in opposite projections of the acceleration according on axes y and z of the two accelerometers. An axial rotation of the head results in opposite projections of the acceleration according to axes x and z of the two accelerometers. The combination of this information with information from the gyro sensor and the magnetic compass, in an embodiment featuring these types of sensors, allows to detect complex posture changes of the user.

A barometric sensor (252) is set on an electronic board (211), according to this example on the electronic board located in the right stem, but alternatively on the electronic board (212) located in the left stem. Such a MEMS sensor can commonly detect a pressure variation of about 6 Pa, which corresponds to a variation of altitude of approximately 20 inches (50 cm). Processing the signal of such a barometric sensor, allows for example to detect a position change of the user, e.g. from a standing position to a sitting or lying position, and vice versa, when said user wears the eyeglasses of the system of the invention.

The risky situations whose detection is aimed by the system of the invention (loss of alertness and falls) are detected by combining information issued from the processed signals of:

the IR receiver (152), excited by the IR transmitter (151); the triaxial accelerometer (251);
and the barometric sensor (252).

The detection reliability is improved by adding to these sensors:

a second IR transmitter and receiver couple;
a second triaxial accelerometer mounted symmetrically to the first on the other stem of the eyeglasses.

The detection reliability is further improved, as well as the capability of discriminating more finely some situations, by adding to the previous sensors:

a gyro sensor;
a magnetic compass;

These last two sensors, are advantageously integrated, alone or in combination, in a MEMS also comprising the triaxial accelerometer.

The processing and calculation unit is advantageously distributed between two modules (261, 262) set respectively on the electronic boards of the right stem and the left stem. As a nonrestrictive example, the module (261) of the right stem comprises a microprocessor and memory means, including a program for acquiring the signals from the sensors, and for processing signals and calculating the relevant parameters, whereas the module (262) of the left stem, collects the signals of the sensors placed on this same stem and their transmission towards the module of the right stem, manages the power supply and the charge of the battery (270) and the communications, whether wired or wireless with other devices, in particular towards a smartphone, a computer, or a WiFi® gateway.

The eyeglasses finally comprise means of alarm distributed between the stems, for example a colored led (282) and a buzzer (281).

According to an embodiment a miniaturized connector (not represented), for example of the micro-USB type is integrated in one the stems and allows data exchange with other devices, via a wire connection, and the recharging of the battery (270).

By using a limited number of sensors and highly integrated electronics, the weight of the eyeglasses of the system of the invention is kept under 1.4 oz (40 grams) without the lenses, with an operating autonomy of at least 8 hours per battery charge.

Advantageously, the eyeglasses of the system the invention comprise foldable stems, in order to be used, carried and tidy up like any conventional eyeglasses, more particularly to allow their tidy up in a case in order to protect the lenses when the user is not wearing said eyeglasses. The distribution of the electronic modules between the right stem and the left stem, implies that the bus connects the electronic boards of the two stems and runs through the hinges of the stems. For this purpose, the eyeglasses of the system of the invention feature specific hinges guiding the bus during the folding and unfolding of the stems so that it follows a high enough radius of curvature avoiding any damage to said bus.

Figure 3:
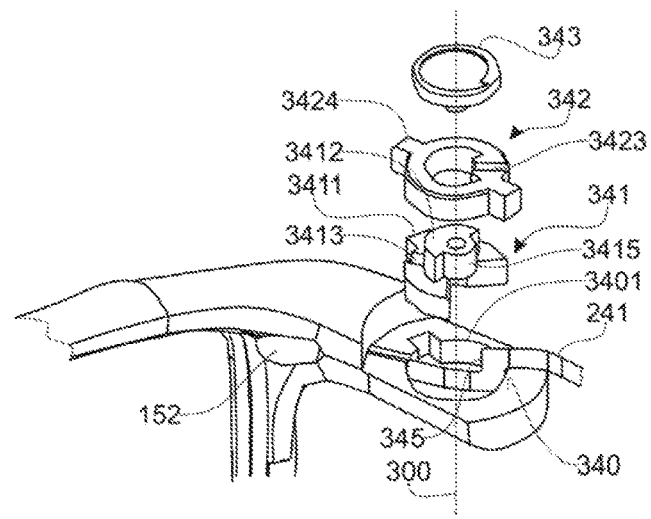
FIG. 3 shows, according to a partial exploded view in perspective, an exemplary embodiment of the hinge of the stems of the eyeglasses of the system according to the invention.

FIG. 3, an exemplary embodiment of the right stem hinge of the eyeglasses of the invention is shown in a position corresponding to the unfolded stem. The stem is supported by a shouldered bearing surface (340) at the end of the rim, making its precise vertical positioning according to the hinge rotation axis (300). The joint is performed between a hub (342) connected to the stem and an axle (341) housed in the fixed part of the frame forming the aforementioned bearing surface (340). The axle (341) comprises two parts connected to each other, the first part (3411) is fitted in a bore (3401) of complementary shape, made in a fixed part of the frame, and the second part (3412), of smaller diameter, around which the hub (342) revolves. The first part of the axle is indexed in rotation in the bore, for example, by means of a tenon and mortise assembly and fixed, for example, by clipsing or gluing. The bus (241) is running in the stem and goes down in the bore (3401) receiving the axle (341) by a shoulder to reach the rim. For this purpose, the first part (3411) of the axle comprises a slit (3413) as a passageway for the bus (241). This first part (3411) of the axle extends on approximately ¾ of a circle the open part providing a clearance equal or slightly higher than 90° for the movement of bus (341) in the bore (3401) when folding and unfolding of the stems. The hub (342) is set up in the stem, and also comprises a slit (3423), as a passageway of the bus part (241) located in the stem behind the shoulder (345), the aforementioned slit (3423) being appreciably diametrically opposed to the slit (3413) of the axle when the stem is unfolded. The aforementioned hub is snapped in a bore of complementary shape, in the stem, indexed in rotation relative to said stem, for example by means of a tenon and mortise assembly, and fixed in said bore, for instance by clipsing or gluing. During the folding of the stem, the part of the bus (241) entering the slit (3413) of the axle does not move, only the part in the slit (3423) of the hub does, up to the bus shoulder (345). The second part (3412) of the axle comprises a portion (3415) of lower diameter than the diameter of the portion guiding the pivot join, the shoulder (345) of the bus glides on this portion of lower diameter during the pivoting of the stem. Thus, the radius of this lower diameter portion defines the radius of curvature imposed on the bus (241) when folding and unfolding the stems. The whole assembly is held in position by a rivet (343). Advantageously, an indexing mechanism is included in the tenon of the axle that stops the axle in rotation in the bore (3401). The hub comprises a tenon (3425) cooperating with this indexing mechanism to index the stem in the unfolded position and to avoid any damaging of the bus (241) by a too important aperture, because the location of the IR receiver (152) does not make it possible to limit this angular displacement by an abutment of the stem on the rim, as that is usually carried out for conventional spectacles.

According to an exemplary embodiment, the eyeglasses of the system of the invention operate in a completely autonomous way, by determining the parameters related to a given risky situation and by generating alarms towards its own means, from an analysis of these parameters performed by the microprogram stored in the processing and calculation unit.

Figure 4:
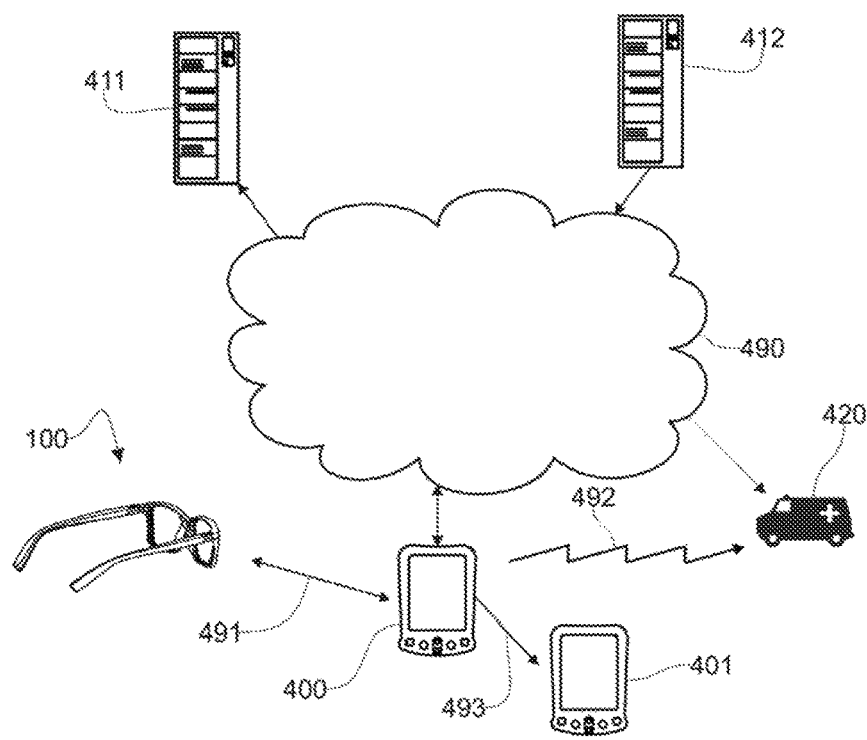
FIG. 4 is a scheme showing an exemplary embodiment of the system of the invention in its so-called connected version.

FIG. 4, according to another embodiment of the system of the invention, the eyeglasses (100) are said connected, and have the ability to communicate either permanently or periodically with another object (400) by a connection (491) either wireless, e.g. of the BLUETOOTH® low energy or ZIGBEE® types, or by wire. As of some examples, the object (400) is a smartphone, a personal computer or a WIFI® gateway. This object (400) is in turn connected to one or more networks, and to other objects (401) or servers (411, 412), for example via internet (490), a cellular network (492) or a proximity wireless link (493) like a Bluetooth® link. This embodiment makes it possible to increase the functionalities of the system. Thus, the connected object (400) is able to download an update of the microprogram from an update server (412) and to upload said update in the processing and calculation unit of the eyeglasses once paired with it. The aforementioned connected object advantageously comprises its own means of calculation and a specific program allowing an analysis of the data collected from the memory means of the eyeglasses, then by analyzing these data, adjusts the eyeglasses operation according to the user, in particular the thresholds of alarms triggering, or the calculation parameters of these thresholds. The same program comprised in the connected object (400) is also able to conduct tests aiming at checking the correct operation of the connected glasses or detecting and fixing malfunctions. For example, when the eyeglasses are comprising two couples of IR transmitter-receiver on each rim, if an abnormal or suspect operation of one of the couples is detected, the assessment of alertness is then based on the sole signals issued by the couple operating correctly. According to a specific embodiment, the connected object (400) is also capable of transmitting alarms to third parties, through various connection routes, such as Internet, a proximity network or cellular network. As a for instance, in the case of a serious fall detection, it sends an alert to a rescue center (420), along with the geolocation of the person wearing the eyeglasses. According to another example of implementation, the connected object (400) sends an alert of reduced alertness of the wearer of the eyeglasses to the smartphones (401) of people in its vicinity. Therefore, the passengers of a vehicle driven by the user are warn about its condition and urge him to stop driving. According to yet another example, the drop of alertness alarm is sent, for example, via a cell phone network or a DECT network, to the remote supervisor of the operator driving a machine or an industrial gear and wearing the eyeglasses. According to this embodiment of the system of the invention the eyeglasses (100) are associated with a single number of identification (UUID) and, through an application set up in the connected object, to information relating to the user, such as its age, its possible pathologies, or information derived from the data acquisition carried out by the eyeglasses, such as its average frequency of spontaneous eye blinking. This information, combined with data from the measurements carried out by the eyeglasses, is transmitted periodically, for example once a day, and in an anonymous way to a server (411) collecting whole of these data. Therefore, this server gradually builds a large database, on which statistical studies implementing artificial intelligence, commonly referred to as the "Big Data", are carried out and used to improve the system and to offer custom updates. Accordingly, the system of the invention implements a machine learning process and adapts specifically to its user. This adaptation comprises two levels. A first level is achieved at the level of the device itself, i.e. the eyeglasses, by implementing its own means of calculation and allows to adapt the conditions of alarm to the own characteristics of the user without changing the processing algorithms. A second level is reached through population analysis and helps to refine the algorithms by detection category and phenotype. This second level is implemented in a remote server (411).

Figure 5:
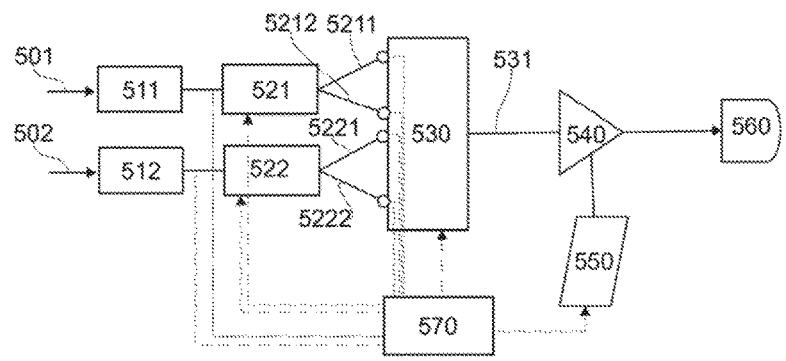
FIG. 5 is a flow chart of an example of signal processing leading to the generation of an alarm.

FIG. 5, according to an exemplary embodiment the generation of an alarm pertaining to a given risky situation, takes into account the signals (501, 502) issued from one or more sensors. The signal issued by each sensor undergoes a filtering step (511, 512) that is specific to each type of sensor in order eliminate the noise and irrelevant influences. During a processing step (521, 522) a series of parameters (5211, 5212, 5221, 5222) is extracted from each signal. These parameters are combined during a calculation step (530) in order to define a composite index (531) relating to the kind of monitored situation. This composite index (531) is then compared (540) with a reference (550) stored in memory, and if it differs from this reference by a significant level, an alarm is generated (560). The steps of processing (521, 522), calculation (530) and comparison (540, 520) implement constants that are stored in the memory means of the processing and calculation unit. Several of these constants are specific to the wearer of the eyeglasses. Therefore, in parallel to the processing of alarms, in the course of a learning step (570), signals and parameters calculated at the processing step (521, 522) are analyzed, and the constants used for processing, calculation a comparison may be changed by an authorized magnitude, in order to adapt to the individual wearing the eyeglasses, this method corresponding to the first level of machine learning and customization of the system of the invention.

Figures 6A, 6B:
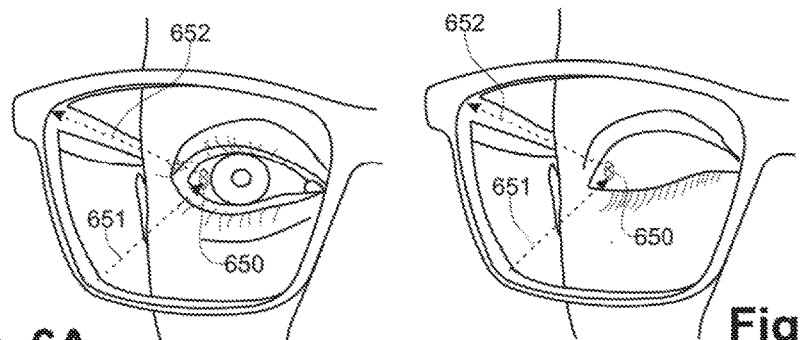
FIGS. 6A-6B show, according to perspective views, the operation of the transmitter and the receiver of the system of the invention, with the eye open in FIG. 6A and with a closed eye in FIG. 6B.

FIGS. 6A-B, the alertness measurement and the related generation of alarms is essentially based on the analysis of the spontaneous eye blinks completed by the detection of head drop. The measurement of eyelid blinks is carried out from the signal issued by the IR receiver. FIG. 6A, when the eye is open, the beam of incident light (651) generated by the IR transmitter is reflected in a light spot (650) on the cornea, the IR receiver measures the intensity of the reflected beam (652). FIG. 6B, when the eye closes, the incident beam (651) is reflected on the eyelid. The reflectance of the eyelid being different from that of the cornea, the light intensity of the reflected beam (652) is different. Thus, the intensity of the reflected signal (652) varies according to the eyelid surface lighted by the bright spot of the incident beam (651). The reflectance of the eyelid is higher than that of the cornea, so the more the eyelid closes the higher the intensity of the reflected signal (652) thus measured by the IR receiver.

Figure 7:
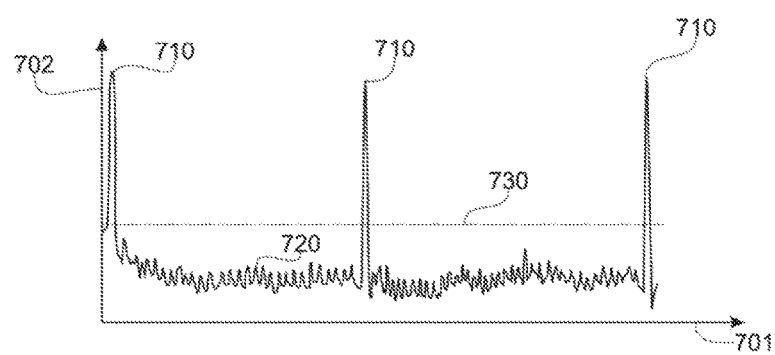
FIG. 7 represents an example of an eye-tracking chart derived from the infrared receiver signal.

FIG. 7 shows an example of the intensity (702) of the signal perceived by the IR receiver vs time (701). Each peak reflects a more or less complete closing of the eyelid. This exemplary diagram makes it possible to distinguish the palpebral movements corresponding to voluntary eye blinks, corresponding to higher intensity peaks, and more numerous peaks, of lower intensity, corresponding to spontaneous eye blinks. Spontaneous eye blinks are fast movements of the eyelid wherein a person is not aware of and whose physiological role is to avoid the desiccation of the surface of the eye by ensuring the collection and the excretion of the tears and the spread out of the lachrymal film. These movements occur according to a variable frequency according to the individual, of about 20 blinks per minute. The frequency and the speed of these blinks are influenced by factors such as the emotional stress, tiredness or the consumption of psychotropic substances, and accordingly constitute indicators adapted to the measurement of alertness. Therefore, for the alertness analysis, only the peaks whose intensity is lower than a threshold (730) are considered. This threshold is set for a given individual, during an adjustment and calibration step of the eyeglasses. According to a specific embodiment, voluntary eye blinks or winks, can be used to control functions, including functionalities of the object connected to the eyeglasses. When implementing such a possibility, only the peaks whose intensity is higher than an intensity threshold (730) and of a duration longer than a given time frame are considered.

Figure 8:
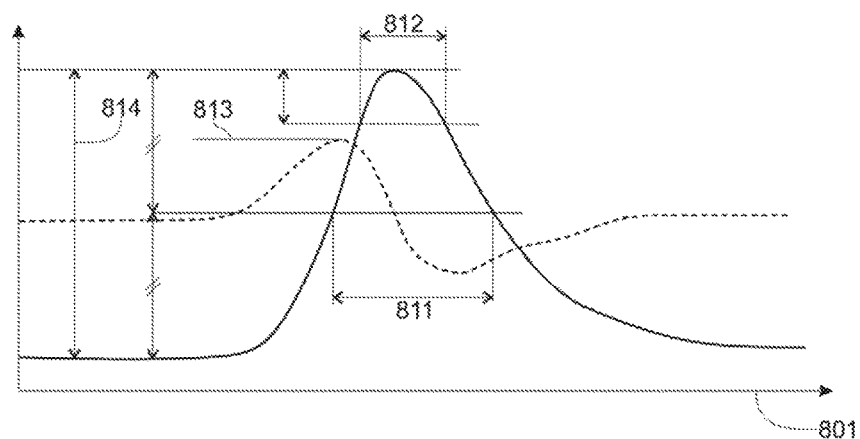
FIG. 8 shows the time evolution of the magnitude of the signal issued by the IR receiver as well as its derivative during a spontaneous eye blink.

FIG. 8, at the scale of a spontaneous eye blink, the analysis of the signal (802) issued by the IR receiver and of its time derivative (803), allows to define several parameters such as:

the blinking duration (811) measured by the peak full width at half maximum or more specifically at the half of its maximum measured intensity;

the duration of closure at more than 80% of the eyelid (812);

the maximum closing speed (813);

Analyzing several peaks over a given time further gives access to:

the spontaneous blinking frequency, or more precisely the number of spontaneous blinking on a given time;

the relative amount of time spent with the eyelid closed at more than 80%.

The beginning of a peak is easily detected on the time derivative of the signal. The derivation operation is however affected by the noise in the signal.

To this end, the signal from the IR receiver, is first filtered in order to eliminate the influence of ambient light, whether natural or artificial. The part of the spectrum of the ambient light falling in the measurement range of the IR receiver affects the response of the sensor by adding noise and additional variation frequencies.

According to an exemplary embodiment, the influence of ambient light is thus eliminated from the signal by applying to this one a moving average polynomial filter, e.g. of the Savitsky-Golay type, followed by a filtering of the signal thus smoothed by a Butterworth's band pass filter, with a 10 Hz bandwidth, centered on the average frequency of spontaneous eye blinking.

The different stages of drowsiness are characterized by an increase in the relative time when the eyelids are closed over a given interpolation time, because of the increase in the eye blink frequency or the increased duration of each eye blink. This feature is captured by the ratio of the total time spent with the eyelid closed at more than 80% (812) over an interpolation duration, further referred as $PERCLOS_{80}$. According to an exemplary embodiment, this parameter is calculated over on interpolation duration of 20 seconds. For an alert individual this parameter is less than 3%. The increase of this ratio indicates the onset of drowsiness and the decrease of alertness. This 3% level is independent of the individual and so enables to reliably characterize a fully alert state of said individual, and to calculate for this state other parameters that better characterize the drowsiness state but are individual dependent.

The analysis of the decrease of alertness performed over a sample of people translates in an increase of the spontaneous eye blink frequency and in an increase of the dispersion of the interval of time between 2 eye blinks, in particular, because the duration of certain eye blinks lengthens. The eye blinking frequency, and the time between two eye blinks, can be extracted from the IR receiver signal over a given interpolation time. However, if this parameter is statistically relevant over a sample of individuals, it is difficult to draw an actual early indicator of reduced alertness for a given individual because the behavior changes from one individual to another. Therefore, such an indicator can be reliably used only for detecting an advanced state of drowsiness, close to a slumber.

For this purpose, an indicator is calculated by considering the proportion of eye blinks having a duration of eye lid closure greater than a given value. As a for instance, this threshold level is set at 0.3 seconds, and if on 10 successive peaks of eye blinks more than 6 have a duration (811), measured by the width of the eye blink peak, longer than this threshold, then the indicator takes the scalar value of 0.6 (6/10). This 0.3 seconds duration and this proportion of 0.6 are high values, corresponding to a state of drowsiness just before falling in a slumber whoever the individual. Therefore, in the same way that the $PERCLOS_{80}$ parameter makes it possible to define, when it is lower than 3%, in a reliable way a fully alert state, the latter parameter, named $DURATION_{50}$, allows when it reaches a level of 0.6 to detect in a reliable way, a state of loss of alertness. The detection of these two extreme values, enables to define other thresholds, by a learning mechanism, related to other parameters that are more sensitive to alertness but more individual dependent.

The AVR parameter is defined by the ratio of the eye blink peak amplitude (814) to the maximum eyelid closing speed (813). This parameter is assessed for each peak of spontaneous eye blink over a given measurement time, e.g. 3 minutes.

Figures 9A, 9B:
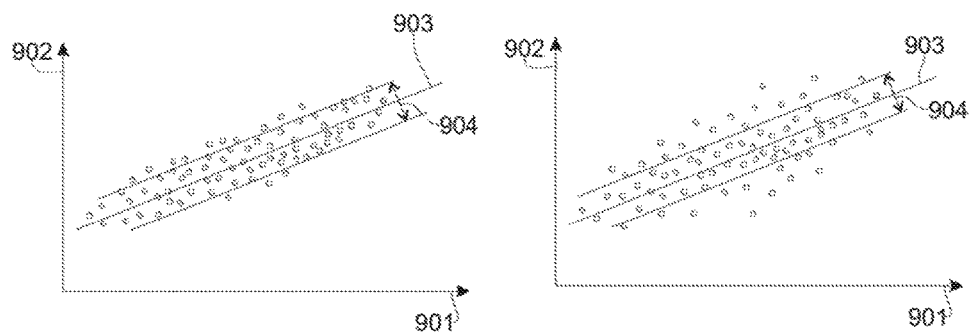
FIGS. 9A-B represent the evolution of the AVR parameter with time, FIG. 9A for an awakened person, and FIG. 9B in the case of a drowsy person.

FIG. 9A, by plotting the successive values (902) of this parameter with time (901) for an alert individual, they line up substantially on a straight line (903). Starting from the dots cloud thus plot, a dispersion interval (904) is estimated for the alert individual, 90% of the cloud being comprised in this interval. The slope of the line and the width of the interval, are individual dependent and for a same individual are likely to vary in time.

FIG. 9B, when the same individual, shows signs of reduced alertness, the variance of the AVR parameter measured over the interpolation time increases, which translates into measurement dots lying outside the interval calculated in the alert state for the same individual. Thus, as a for instance, a scalar index of drowsiness/alertness is obtained by counting the number of times the assessed AVR value is out of the interval, over a given time, said interval boundaries being calculated when the individual is in an awakened state. The interval must be calculated for each individual. For example, the line (903) equation and the interval (904) are calculated from the most recent AVR values that were assessed when the individual was in a confirmed awakened state, i.e. with a $PERCLOS_{80}<3\%$, the corresponding data are stored and updated in the memory means of the processing and calculation unit.

Additional parameters derived from the accelerometer signal allows to detect and to characterize a head drop, its associated frequency or duration, these parameters being characteristic of an advanced drop of alertness.

According to an exemplary implementation, only the acceleration according to the direction of gravity is used, that is to say according to they axis in the embodiment shown FIG. 2.

In normal circumstances, the accelerometer measures an acceleration of 1 G directed according to the positive direction of the y axis and corresponding to the gravity.

Figure 10:
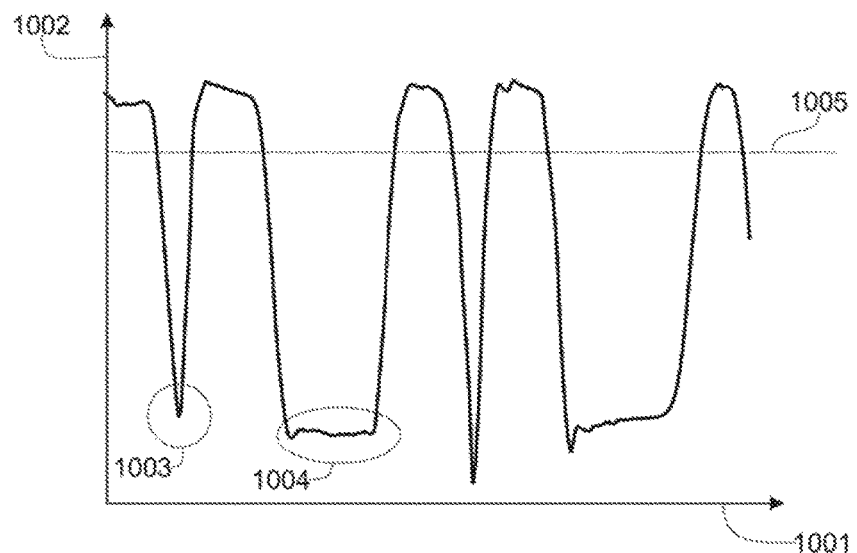
FIG. 10 shows an example of the evolution of the acceleration measured according to the direction of gravity during a head drop.

FIG. 10, on a diagram showing the variation of the acceleration on they axis (1002) vs time (1002), at the time of a significant drop of alertness (1003, 1004) translating in a micro slumber, the head of the individual falls forwards according to the neck joint of least resistance. In the extension position, with the head leaning forward, the orientation of they axis compared to gravity makes that the projection of gravity acceleration on this axis is lower than 1 G, and then reaches 1 G again if the individual straightens its head. Therefore, a head drop (1003, 1004) is detected if the acceleration according to the axis y takes a value that is less than a threshold value (1005). The signal is initially filtered by a low pass filter, with a cut-off frequency of about 2 Hz in order to remove from the signal the shakes related to the activity of the individual. Only a head drop lasting over significant duration is taken into account, e.g. lasting more than 0.2 second. Thus, a scalar parameter is for example determined by the number of head drop found over a given measurement time. A second scalar parameter corresponds to the number of head drop lasting more than a second and longer duration threshold (1004), for example longer than 0.5 or 1 second, counted over the same measurement time interval or a longer time interval.

These scalar parameters:
PERCLOS$_{80}$, v1(t)
DURATION$_{50}$, v2(t)
number of APR points outside the forecast range, v3(t)
number of head drop and long-lasting head drop v4(t), v5(t)

where t is the time, are calculated in real time and are combined into a composite index that reflects the state of alertness of the individual and from which the decision to generate an alarm is made.

The calculation principle of the composite index is similar whatever the type of risky situation whose detection is aimed, but uses different parameters depending on the type of detection sought. According to an exemplary embodiment and depending on the nature of the detection sought, these parameters are whether scalar or binaries, in the latter case taking the value 0 or 1 (or −1, +1) depending on whether a specific pattern is detected or not in the signal.

Accordingly, the parameters issued from the signals processing, whether scalar or binaries, are functions of time and noted v1(t) . . . $v_n$(t).

They are grouped in a M(t) vector:

$$M(t) = \begin{bmatrix} v_1(t) \\ \vdots \\ v_2(t) \end{bmatrix}$$

A severity composite index V(t) related to a risky situation is e.g. defined as:

$$V(t)=A \cdot V(t-1)+B \cdot M(t)$$

Where A and B are matrices of coefficients which are specific to the individual and that are weighting the influence of each parameter relative to one another. According to a simple example of implementation, at the beginning ($t_0$):

$$V(t_0) = V_0 + B \cdot M(t_0)$$

$$B = \begin{bmatrix} \beta_{11} & \cdots & \beta_{1n} \\ \vdots & \ddots & \vdots \\ \beta_{n1} & \cdots & \beta_{nn} \end{bmatrix}$$

$$A = [\alpha_1 \ \cdots \ \alpha_n]$$

and V(t) is a scalar.

The $\alpha_i$ and $\beta_{ij}$ factors as well as the equation used for the combination of the parameters for the calculation of the composite index, evolve with the machine learning process, notably by the data statistical analysis performed at the server level (411, FIG. 4).

Based on the level of the composite index, several alarm levels are triggered. Coming back to FIG. 2, a first level of alarm corresponding e.g. to an early stage of alertness drop, leads to the light up of the led (282) either continuous or blinking. A second alarm level corresponding to a further loss of alertness, triggers the buzzer. A third level activates simultaneously the led and the buzzer, and if the system is configured to do so, sends a message to the connected devices in proximity with the connected object paired with the eyeglasses.

Figure 11:
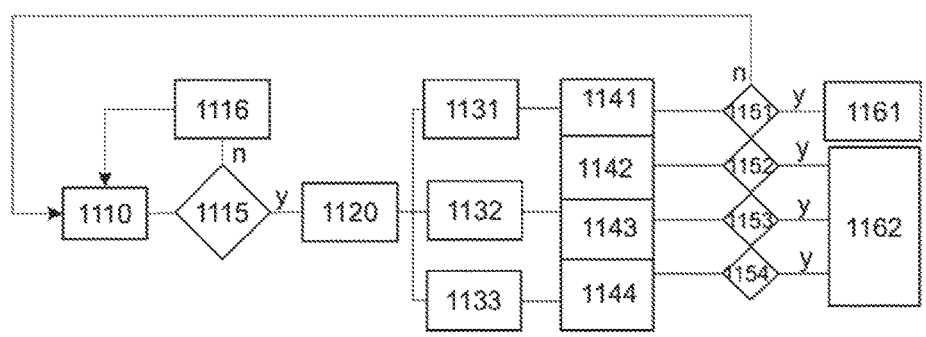
FIG. 11 is a flow chart of an exemplary signals processing and alarm triggering according to the method of the invention.

FIG. 11, according to an exemplary embodiment, the method of the invention comprises a first step (1110) for checking out the actual wearing of the eyeglasses. This step aims at ensuring the consistency of the further processing carried out, but also to turn the eyeglasses into a sleep mode if they are not used, in order to reduce the electrical consumption. This check out step, uses only the signal issued by the IR receiver using a specific filter and a specific processing. If the result of the checkout test (1115) is negative, the eyeglasses are turned (1116) in a sleep mode. While in sleep mode, a check out test is performed on a regular basis, for example every minute, in order to activate the active mode, if the eyeglasses are detected as worn by the user. If the eyeglasses are detected as worn by the user, the signals acquisition (1120) is launched, this acquisition includes filtering operations specific to each signal. The acquisition is carried out at a sampling frequency ranging from 50 Hz to 150 Hz preferably around 70 Hz, who turns out to be a frequency to collect enough data to make the appropriate processing, while limiting the electrical consumption. The signals thus conditioned are sent to processing modules (1131, 1132, 1133) which extract from said signals the specific and representative parameters either scalar or binaries. Thus, according to an exemplary embodiment, one of the modules (1131) is dedicated to the extraction of the parameters derived from the signal issued by the IR receiver. Another module (1132) is dedicated to the extraction of the parameters from the signals issued by the accelerometers and a third module (1133) is dedicated to the extraction of the parameters from the signal issued by the barometric sensor. The parameters resulting from this processing are combined in composite indexes, during a calculation step also implementing several modules, for example, a module for the calculation of alertness (1141) using the parameters derived from the processing of the signal issued by the IR receiver and at least one parameter resulting from the processing of the signal issue by the accelerometer, a module of calculation (1142) relating to the falls using the parameters resulting from the processing of the accelerometry signals and, according to a specific embodiment, those derived from the processing of the signal issued by the barometric sensor, a module of calculation (1143) relating to the falls known as soft, using parameters resulting from the processing of accelerometry and barometric sensor signals, and a module of calculation (1144) relating to the recovery after a fall, using the parameters resulting from the processing of the accelerometry signals, the IR receiver signal and the signal from the barometric sensor. Each module of calculation thus defines a composite index relating to the risky situation whose detection is aimed. Each of these composite indexes is compared to a threshold value that is stored in memory, that is to say an alertness test (1151), a fall test (1152), a soft fall test (1153) and a recovery after fall test (1154). If the threshold value is passed an alarm request is addressed to an alarm management module (1161, 1162). According to this example, two alarm management modules are used. An alarm management module (1161) relating to alertness, that triggers an alertness alarm according to an alertness composite index as described above. An alarm management module (1162) relating to falls, which depending on the passing of a threshold pattern of the 3 composite indexes related to falls, triggers various means of alarm, considering all or part of the composite indexes of fall, soft fall, and recovery after fall. If no threshold is passed, the acquisition and processing of the signals continue without change until a possible detection of an alarm condition. Therefore, starting from a common acquisition basis, carried out with a limited number of sensors and of processing modules (1131, 1132, 1133), the functionalities of the system are adapted to the needs by activating or loading the specific calculation and alarm management modules.

As a for instance, if the user system of the invention is young, healthy and not working in a dangerous environment, the main targeted feature is alertness monitoring, for example when driving. In such a case, the modules relating to the calculation and the alarm management relating to falls (1142, 1143, 1144, 1152, 1153, 1154, 1162) are not activated, although the information derived from the accelerometers remains used, in particular for the detection of a head drop. To the opposite, for an older person, not driving, the main risk to be covered is that of the fall. In such a case the alarm management modules relating to alertness (1141, 1151, 1161) are not activated, which however does not mean that information resulting from the IR receiver is not used, they are indeed used in the calculation module (1144) dealing with the recovery after fall. Finally, for other specific cases, whole of the modules is activated.

Figure 12A:
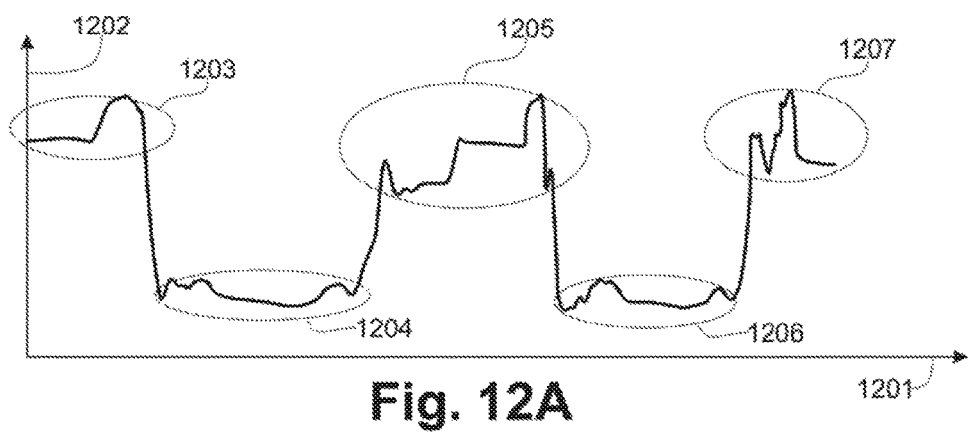
FIGS. 12A-B show the evolution of the signal issued by the IR receiver during wearing and take off of the eyeglasses of the system of the invention, in FIG. 12A the raw signal, and in FIG. 12B, the filtered signal and its time derivative.
Figure 12B:
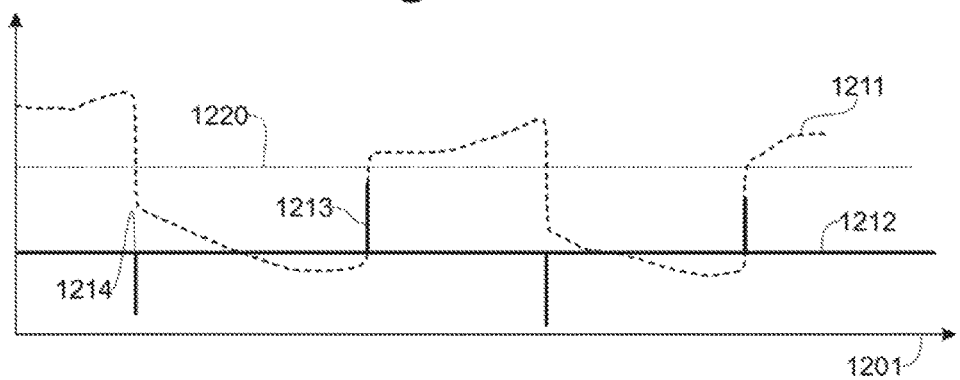

FIGS. 12A-B, signals from the IR receiver are used to check out if the user actually wears the glasses.

FIG. 12A, when following the evolution of the intensity (1202) of the signal emitted by the IR receiver according to time (1201) during successive putting and withdrawal of the eyeglasses, when the glasses are removed (1204, 1206), the emitted infrared beam is not reflected by the eyelid or the cornea and the signal intensity is low. On the other hand, as soon as the glasses are correctly worn (1203, 1205, 1207) by the user the reflection of the signal on the ocular area clearly increases the intensity of the signal.

FIG. 12B, according to an exemplary embodiment, in order to detect if the user is wearing or not the eyeglasses, the signal issued from the IR receiver is strongly smoothed (1211) for example by means of an exponential weighting moving average filter. Using the time derivative (1212) of the filtered signal makes it possible to easily detect an event of withdrawal (1214) or putting on (1213) of the eyeglasses. Alternatively, or in a complementary way, a threshold (1220) is defined so that the glasses are correctly worn by the user when the intensity of the signal (1211) thus strongly filtered, takes values higher than this threshold (1220). When the user does not wear the eyeglasses, for instance because they fell down following a fall, or when it does not wear them correctly, for example too ahead on the nose or when they do not rest on the two ears, the calculation of parameters, not only those issued from the IR receiver signal but also derived from the signals issued by the other sensors is erroneous. Therefore, the actuation of the sleep mode following the detection of the user not wearing or not properly wearing the eyeglasses is progressive and starts with the emission of a specific alarm, e.g. on the led and the buzzer and possibly on the connected object paired with the glasses. Then, during the periodic tests performed in the sleep mode, a short alarm is triggered if the glasses are still detected as not worn or incorrectly worn by the user, for example by a brief and simultaneous triggering of the led and the buzzer, for each test performed e.g. within 15 minutes after the actuation of the sleep mode. Beyond this period, the system shifts to a deeper sleep mode where no alarm is triggered FIGS. 13A-B, for the detection of simple falls, the calculation of relevant parameters uses the accelerometer signals. The signals are initially filtered through a low pass filter with a low cut-off frequency, e.g. 0.1 Hz, in order to eliminate vibrations and phenomena corresponding to everyday life activities. According to an exemplary embodiment, a second filtering such as a moving median filter, preferentially of 3rd order, is performed, this type of filter makes it possible to eliminate the random noise while preserving the peaks acuity. FIG. 13A, taking into account the positioning of the accelerometer, the gravity being directed according to the positive y axis, a first major effect of a fall is detected by a drop of the acceleration measured according to the y axis which is also detected on the sum of accelerations according to the three axes. Thus, by plotting the evolution of the sum of accelerations (1302) according to the 3 axes of the accelerometer vs time (1301), a fall event is characterized by the appearance of a first peak (1303) directed in the negative direction and corresponding to the free fall phenomenon. That first peak is almost immediately followed by a second peak (1304) directed in the positive direction of the axis (1302) and corresponding to the impact of the body on the ground or on any other obstacle. Therefore, the appearance of two consecutive inverted peaks in the sum of accelerations, in a given time window, each exceeding a threshold (1305, 1306), is a specific pattern indicative of a fall. As a for instance, the lower threshold value is set at 0.6 G (5.89 m·s$^{-2}$) and the upper threshold (1306), corresponding to the impact, is set at 2 G (19.62 m·s$^{-2}$). These values are not user dependent and lead to a parameter of the binary type, translating whether or not such a pattern is detected over a given measurement time. With these threshold values, everyday life activities such as walking or stepping down a stairway do not generate a detectable pattern and thus do not generate any false alarm.

FIG. 13B shows evolution (1312) of the time derivative of the signal issued by the barometric sensor vs time during a fall event followed by a recovery where the person raises up again. A first peak (1313) corresponds to the fall, i.e. an altitude drop resulting in an increase in the measured atmospheric pressure. The individual then remains on the ground for a certain time, thus the pressure stabilizes, then it raises up, which corresponds to a second peak (1314) of reduction of the pressure, or increase in altitude. These events occur over a longer time than the succession of acceleration peaks observed during a fall event. Therefore, a fall event is also characterized by a binary parameter, corresponding to the appearance of a positive peak (1313) in the time derivative of the barometric pressure whose amplitude exceeds a certain threshold. Three feet (1 meter) free fall implies a pressure variation of 12 Pa over a duration of approximately 0.3 seconds. Actually, a fall is rarely completely free so that the threshold is, for example, set between 10 Pa·s$^{-1}$ and 20 Pa·s$^{-1}$. The corresponding characterization parameter is a binary parameter whose value depends on whether or not such a positive peak is observed over a given measurement time. The recovery after the fall can be detected by the appearance of a second peak (1314) inverted when compared to the first and which amplitude exceeds a threshold value, for example comprised between 5 Pa·s$^{-1}$ and 10 Pa·s$^{-1}$. So, an additional parameter for the characterization of a fall is a binary parameter, indicating the presence of a recovery peak on the time derivative of the pressure signal in a given interval of time following the fall peak. Finally, an additional parameter, of scalar type, corresponding to the time (1317) separating the fall peak (1313) from the recovery peak (1314) on the time derivative of the pressure signal is also used to characterize the seriousness of a fall. These parameters are combined into a composite index according to a similar principle to the one exposed for the measurement and detection of the loss of alertness, which composite index is used to trigger different levels of alarm.

The method exposed above is effective for detecting a fall involving an even short free fall phenomenon, found in the case of an accidental fall or in the case of a sudden loss of consciousness. However, in certain circumstances or for some people at risk, the fall can be caused, for example, by a progressive loss of consciousness, leading to a fall, known as a soft fall, not allowing to detect a free fall phenomenon. However, this type of fall is critical for some people at risk. If a free fall event can be detected by the peak (1303) directed according to the negative y axis, such a peak is not generally seen in the case of a soft fall, the peak of impact (1304) is however detected, although with a lower amplitude than in the case of an accidental fall. The same applies for the signal corresponding to the time derivative of the barometric pressure, a peak (1313) corresponding to the altitude drop is well observed but less salient in case of a soft fall. Therefore, a soft fall is characterized by the appearance of an impact peak, detected on the sum of accelerations, with a lower threshold as compared to the case of a free fall, and by a positive peak in the time derivative of the pressure signal, also detected considering a lower threshold value. These two parameters are binary parameters reflecting the appearance of such peaks in the measurement interval.

However, using only these two parameters with lowered thresholds leads to a risk of detecting a negative false, i.e. to interpret as a fall a situation of the everyday life, like sitting down on a chair or in an armchair.

FIG. 14, to the difference of an everyday life situation like sitting down in an armchair, a fall, even a soft fall, implies a loss of verticality. The position of the glasses, on the head of the individual, is particularly advantageous to measure such a loss of verticality. The loss of verticality is measured for example by the value of the resulting acceleration in a plane perpendicular to the gravity, that is to say on the x and z axes while referring to FIG. 2. Thus, the plot of the intensity of acceleration (1402) in a plane perpendicular to the gravity vs time (1401) during a soft fall event, clearly reveals one or more peaks (1403) higher than a threshold (1404) which are thus detectable and whose detection over the acquisition time is captured in a binary parameter. These various parameters are combined in a composite index in order to detect a soft fall and to generate an alarm.

However, the combination of these parameters still does not make it possible to detect and characterize a soft fall during which the head remains appreciably vertical, as it is the case for a fall whereas the subject is leaned against a wall, or of another complex situation, leading to a negative or a positive false.

In order to cure these deficiencies, the complete algorithm for the detection and the characterization of the falls takes into account parameters determined in the moments following the fall and which generally attests of the recovery, or not, of the victim. These parameters allow, among other things, to reduce the rate of negatives false, more specifically in case of soft fall, by avoiding the generation of alarms and the notifying of rescue services in situations that are not justified.

As a for instance, in addition to the time separating the fall from a potential recovery as defined in FIGS. 13A-B, a serious soft fall translates, for example, by a loss of consciousness of the individual. Such a loss of consciousness can be captured, in particular, by:
the individual remains staying in a non-conventional posture;
the individual does not exhibit a significant activity
the eyelid activity of the individual corresponds to a serious loss of alertness.

The posture of the individual can be determined for example by the values of the acceleration on the different axes of the accelerometer. When the person is motionless or quasi motionless the accelerometer is only subjected to the action of the gravity, which projects according to the positive y axis of FIG. 2 when the head is straight. Therefore, by measuring the acceleration components according to the 3 axes of the accelerometer, the orientation of the head is given. This orientation is defined by an angle compared to the theoretical vertical position of the head. The value of this angle is a scalar parameter, symptomatic of the posture of the individual after a fall.

The activity of the individual after a fall is also measured considering the signal issued by the accelerometer. If the individual moves, acceleration variations are observed. Therefore, the variation magnitude of the accelerations over a given time frame, measured for example by the variance of the acceleration signal over this time frame, is a symptomatic scalar parameter of the activity of the individual.

The measurement of the eyelid activity and the parameters which are deduced from it has been presented above.

Of course, the calculation of the activity parameters following a fall is not limited to the case of a soft fall but is also relevant in the event of an accidental fall.

The various parameters are combined in a composite index, according to the method exposed previously, the level of which is used to decide of the triggering of alarms.

In a specific but not exceptional case, the eyeglasses fall down from the head of the individual upon the fall, or stay in an incorrect position on its face during a time following the fall. In such a case, even if a fall signature can be detected, the parameters characterizing the fall by the behavior of the individual in the moments following the fall are not measurable, or are measured in an erroneous way. Thus, according to an exemplary implementation, following the detection of a fall, the generation of an alarm based on the parameters assessed after the fall event comprises a check out of the correct wearing of the eyeglasses by the individual If a not wearing or an incorrect wearing is detected, an alarm is generated and repeated during a defined time, as long as the glasses are not put on correctly. If after this defined time, in spite of the emission of the alarms, the eyeglasses are still not correctly worn, then it is possible that the person is not able to put them on back, and an alarm is triggered.

Before being capable of being used effectively, the eyeglasses of the system of the invention must be adapted to their user.

This adaptation comprises a mechanical adaptation, in particular of the stems, and a calibration of the sensors, more particularly of the accelerometer and of the IR receiver.

The calibration is carried out by a professional, for example an optician, or by the user himself, guided by an application set up in the smartphone connected to the glasses.

The accelerometer calibration, aims to determine accurately the gain on each of the axes and the rotation matrix so that the acceleration of the gravity is oriented according to the y axis when the user wears the glasses in a way considered to correspond to a vertical position of the head. According to an exemplary embodiment, this calibration is performed using 3 acquisitions done in defined configurations. According to a first configuration, the eyeglasses are placed perfectly horizontal, in position corresponding to the wearing position, for example in a bracket that is specially adapted for this purpose. In such a circumstance the y axis is supposed to measure a positive 1 G acceleration. According to a second configuration, the eyeglasses are placed perfectly horizontal, in a position that is reversed from the wearing position, for example in a specific bracket. In such a circumstance they axis is supposed to measure a negative 1 G acceleration. In a specific embodiment the brackets used for these operations are part of the eyeglasses packaging. In a third configuration the glasses are worn by their user in a right head position. The analysis of the three measurements carried out under these conditions makes it possible to caliber the accelerometer.

The calibration of the IR receiver consists in particular to set the threshold that allows to discriminate voluntary eye blinks from spontaneous eye blinks. According to an exemplary calibration method, the user wears the eyeglasses for a fixed period, e.g. 1 minute, during which it performs successive voluntary eye blinks at defined time intervals, e.g. every 10 seconds. During the acquisition phase, the system adjusts its setting, in order to detect 6 voluntary eye blink peaks and from 10 to 20 peaks of spontaneous eye blinks. The method may be repeated several times in order to check out the correct adjustment.

These calibration operations are advantageously carried on a periodic basis.

Figure 15:
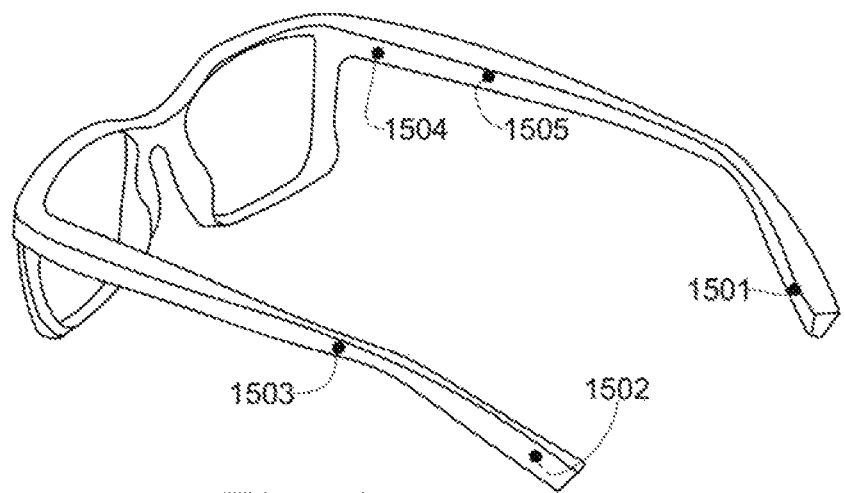
FIG. 15 shows, according to a perspective view, an exemplary embodiment of the arrangement of additional sensors in an enhanced version of the eyeglasses of the system of the invention.

FIG. 15, according to a specific embodiment, the eyeglasses of the system of the invention comprise additional sensors. This enhanced version allows to detect other risky situations. This paragraph and FIG. 15, only quote the sensors not previously described. As an exemplary embodiment the enhanced version comprises:
- a thermometer (1501) to measure the body temperature;
- a heart pace sensor (1502).

These two sensors are advantageously placed on the stem ear pieces, behind the ears, for more reliable measures.
- a microphone (1503);
- a blood pressure sensor (1504), coming in contact with the temple of the user;
- the heart pace sensor (1502) is advantageously equipped with a photodiode to measure the blood oximetry.
- a blood glucose sensor (1505), for example, an infrared sensor measuring the glucose level in the blood through the skin.

The description above and the exemplary embodiments show that the invention achieves its goal, namely to propose a customized system for monitoring the occurrence of a risky situation, using a discrete and aesthetic sensor.

The invention claimed is:

1. A method for detecting a situation threatening an individual and implementing a system comprising a plurality of sensors; an alarm; eyeglasses comprising hinged stems; a triaxial accelerometer; an IR transmitter; an IR receiver; a barometric sensor; and a processing and calculation unit comprising a microprocessor and a memory; wherein the processing and calculation unit is configured to execute a computer program to analyze data issued by said plurality of sensors and to trigger the alarm based on a result of the analyzed data; and wherein said plurality of sensors being set up in stems and rims of the eyeglasses and being connected to the processing and calculation unit, the method comprising any combination of steps consisting of:
   a) controlling the IR transmitter, and collecting and processing signals received from the IR receiver to detect that the eyeglasses are worn by a user;
   b) controlling the IR transmitter, and collecting and processing the signals received from the IR receiver to measure a state of alertness of the user, wherein the processing of signals received from the IR receiver comprises steps of filtering of the signals collected from the IR receiver to eliminate influence of ambient light on the signals from the IR receiver and calculating a composite alertness index, used to trigger an alertness alarm, by combining alertness parameters comprising:
      (i) a relative duration of masking of an eye of a user by user's eyelid on a first predetermined time;
      (ii) an average time interval between two successive eye blinks, over a second predetermined time, in relation to a first reference that is specific to the user;
      (iii) scattering of a ratio between a closing magnitude and a closing speed of the user's eyelid, over a third predetermined time, in relation to a second reference that is specific to the user; and
      (iv) a proportion of eye blinks whose duration exceeds a predetermined certain threshold, over a fourth predetermined time;
   c) collecting and processing signals received from the triaxial accelerometer to detect a fall;
   d) collecting and processing signals received from the barometric sensor in combination with the processing of signals collected from the triaxial accelerometer to characterize the fall; and
   e) generating an alert in response to results of step b), step c) or step d).

2. The method according to claim 1, wherein the step of filtering in step b) consists of applying a moving average polynomial filter followed by a band pass filter to the signals collected from the IR receiver.

3. The method according to claim 1, wherein the first and the second references specific to the user, are calculated from the collection and the processing of the signals received from the IR receiver, and assessed in response to specific conditions involving the alertness parameter (i) or (iv) being met.

4. The method according to claim 1, wherein the step e) comprises triggering the alertness alarm whose level is conditioned on the results of the steps b) and c).

5. The method according to claim 1, wherein the processing performed at the steps c) and d) generate a composite index of a severity of the fall, used to trigger a fall alarm, based on fall parameters comprising: an acceleration magnitude combined along three axes of the triaxial accelerometer; a variance of the acceleration magnitude parameter over a predetermined duration; and an acceleration component over an axis of the triaxial accelerometer parallel to a direction of gravity.

6. The method according to claim 5, wherein the fall parameters further comprise: a magnitude of acceleration, combined over the axes of the triaxial accelerometer in a plane perpendicular to the direction of the gravity; and a variation of a barometric pressure between two moments.

7. The method according to claim 6 wherein the trigger of the fall alarm is conditioned by a level of the fall parameters assessed after a detection of the fall.

8. The method according to claim 7, wherein the fall parameters assessed after the detection of the fall comprise: an assessment of the state of alertness according to the step b); a measurement of a posture of a user using the signals collected from the triaxial accelerometer or the barometric sensor; and determining a time spent on the ground, using the signals collected from the triaxial accelerometer and the barometric sensor.

9. The method according to claim 1, wherein the processing and calculation unit of the system is borne by the eyeglasses; wherein the alarm comprises a color LED or a buzzer, installed in the eyeglasses; and wherein the alert generated in step e) triggers the alarm set in the eyeglasses.

10. The method according to claim 1, wherein the system further comprises a remote unit; and wherein the eyeglasses comprise a wireless transmitter/receiver configured to exchange information with the remote unit, the remote unit being itself connected to one or more networks; and wherein step e) further comprises a step of transmitting the alert by the remote unit to though said one or more networks.

11. The method according to claim 10, wherein the remote unit is a smartphone; and wherein step e) further comprises a step of transmitting alert to other smartphones in a vicinity of the remote unit.

12. The method according to claim 1, wherein the processing and calculation unit of the system comprises a connection facility to connect to Internet; wherein the system further comprises a central server to exchange information with the processing and calculation unit over the Internet; and wherein information collected in one of steps b), c) or d) are recorded in the memory of the processing and calculation unit and transmitted to the central server on a periodical basis.

* * * * *